United States Patent
Parkinson

(10) Patent No.: US 9,692,217 B2
(45) Date of Patent: Jun. 27, 2017

(54) TUBE AND CONDUCTOR SET

(71) Applicant: Sunlite Plastics, Inc., Germantown, WI (US)

(72) Inventor: Michael Parkinson, Germantown, WI (US)

(73) Assignee: Sunlite Plastics, Inc., Germantown, WI (US)

( * ) Notice: Subject to any disclaimer, the term of this patent is extended or adjusted under 35 U.S.C. 154(b) by 0 days.

(21) Appl. No.: 15/190,811

(22) Filed: Jun. 23, 2016

(65) Prior Publication Data

US 2017/0063060 A1    Mar. 2, 2017

Related U.S. Application Data

(60) Provisional application No. 62/212,791, filed on Sep. 1, 2015.

(51) Int. Cl.
| | | |
|---|---|---|
| *H01B 7/00* | (2006.01) | |
| *H02G 3/04* | (2006.01) | |
| *H01B 3/44* | (2006.01) | |
| *H01B 13/00* | (2006.01) | |

(52) U.S. Cl.
CPC .............. *H02G 3/0481* (2013.01); *H01B 3/44* (2013.01); *H01B 7/0072* (2013.01); *H01B 13/0036* (2013.01)

(58) Field of Classification Search
CPC ...... H02G 3/0481; H02G 3/0487; H02G 3/00; H02G 3/02; H02G 3/04; H02G 3/0406; H02G 3/0437; H01B 13/34; H01B 7/0072; H01B 7/0081; H01B 13/0036; H01B 3/00; H01B 13/004; H01B 13/012; H01B 3/44

USPC .......... 174/19, 68.1, 68.3, 72 A, 113 R; 128/200.24, 200.26, 897, 899; 604/523, 604/264, 96.01; 138/111, 118, 118.1
See application file for complete search history.

(56) References Cited

U.S. PATENT DOCUMENTS

| | | | | |
|---|---|---|---|---|
| 3,383,456 A | * | 5/1968 | Kosak | H02G 3/0462 174/117 R |
| 3,580,983 A | | 5/1971 | Jackson | |
| 4,381,208 A | | 4/1983 | Baverstock | |
| 4,758,298 A | | 7/1988 | Goorsky et al. | |
| 5,439,720 A | | 8/1995 | Choudhury | |
| 5,607,528 A | | 3/1997 | Choudhury | |
| 6,434,430 B2 | * | 8/2002 | Borgersen | A61N 1/056 607/122 |
| 7,402,754 B2 | * | 7/2008 | Kirwan, Jr. | A61B 18/12 174/110 R |

(Continued)

*Primary Examiner* — Angel R Estrada

(74) *Attorney, Agent, or Firm* — Quarles & Brady LLP

(57) ABSTRACT

A tube and conductor set includes a polymeric tube having a radially outward facing surface and a conductor having a polymeric sheath in which the polymeric sheath has a radially outward facing surface. The radially outward facing surface of the polymeric tube is bonded to the radially outward facing surface of the polymeric sheath of the conductor over an axial length, except for one or more unbonded intermediate axial gaps. These one or more unbonded intermediate axial gaps provide a starting point for the separation of one of the ends of the polymeric tube from one of the ends the conductor. It is contemplated that more than one tube and/or conductor can be bonded and that each line of bonding could have such unbonded intermediate axial gaps to facilitate ease of separation.

21 Claims, 2 Drawing Sheets

(56) References Cited

U.S. PATENT DOCUMENTS

| | | | |
|---|---|---|---|
| 8,408,210 B2* | 4/2013 | Curley | A61M 16/04 128/207.15 |
| 8,497,425 B2* | 7/2013 | Morrow | H02G 3/06 174/68.1 |
| 8,568,316 B2* | 10/2013 | Finneran | A61B 5/14503 128/207.14 |
| 2009/0209940 A1 | 8/2009 | Nimkar et al. | |

* cited by examiner

TUBE AND CONDUCTOR SET

CROSS-REFERENCE TO RELATED APPLICATION

This application claims the benefit of U.S. Provisional Patent Application No. 62/212,791 filed Sep. 1, 2015, which is hereby incorporated by reference for all purposes as if set forth in its entirety herein.

STATEMENT OF FEDERALLY SPONSORED RESEARCH OR DEVELOPMENT

Not applicable.

TECHNICAL FIELD

This disclosure relates to tube and conductor sets for use in medical devices such as, for example, suction and irrigation systems employed in medical procedures.

BACKGROUND

Tube and conductor sets are used in many medical devices to provide fluid and electrical communication between device components.

The tube or tubes can provide a channel or passageway for the transport of fluids (either gases or liquids). As one example, sterile saline fluid may be supplied by a first tube to irrigate a surgical region, while a second tube may provide a vacuum to suction and collect the fluid periodically either during irrigation or after irrigation.

Depending on the particular medical device, the tubes may connect a tool portion of the medical device, which is temporarily received at the surgical site in the patient's body, to a pump or other external part of the device and/or to a supply connector built into the wall of a hospital or another fluid or vacuum source.

In many instances, these tube sets are constructed to also have an electrical conductor or conductors (sometimes called a multi-conductor when the wires are bundled together) that run in parallel with the tube or tubes. The electrical conductor or conductors may be used to communicate electrical signals between respective portions of the medical device. For example, the tool end of the device may be held by the physician and controls on the tool end may be manipulated by the physician in order to indicate to the connected pump via the conductor or conductors that saline should be provided or a vacuum should be drawn.

The production of such combined tube and conductor sets is conventionally a continuous process in which one or more tubes are extruded and fused together with the one or more conductors. Then, either a spool of the tube and conductor set or a shorter pre-cut length is supplied to the device manufacturer.

During further assembly of the medical device, an assembler typically takes each of the ends of the cut lengths and tears or peels apart the tube(s) and conductor(s) from one another to separate them from one another. These separated ends can then have connectors attached to them and be further installed in the medical device.

SUMMARY OF THE INVENTION

It is not a trivial process to separate the tube(s) and conductor(s) from one another at the ends of the set. The step of manual separation of the ends can be both tedious and repetitive, as the assembler must pinch the ends of the tube(s) and conductor(s) and then, using an appreciable amount of force, separate the bonded segments from one another. Among other things, this adds time to the production process and can require operators to take periodic breaks to rest their fingers. Although the ends of a given length might be supplied in a pre-separated state from the manufacturer of the tube and conductor set, if the ends are already separated and free prior to shipping, then the separated ends are particularly prone to pinching or other damage that can result in damaged product that cannot be used in product.

An improved tube and conductor set is disclosed herein with a structure that can enable easier separation of the tube(s) and conductor(s) from one another at the ends of the length. This can make it physically easier for the tubes and conductor to be separated from one another by the assembler, thereby reducing assembly time and improving the ergonomics of the separation process. In short, the tube and conductor set can include an intermediate unbonded gap in a region which normally bonded between a tube and a conductor (and potentially also an intermediate gap between a tube and another tube) between a pair of adjacent bonded lengths. A user can easily place his or her fingers between the unbonded gaps to separate the tube(s) and conductor(s) from one another and then more easily pull the tube(s) and conductor(s) apart to separate the ends of the tube(s) and conductor(s) for the attachments of connectors or terminals. This design is more ergonomic and effective than the traditional pinch and pulling action that must be performed to separate the ends of tube(s) and conductor(s) that are bonded over their entire axial lengths.

According to one aspect of the invention, a tube and conductor set is provided which includes one or more polymeric tubes and one or more conductors. Each polymeric tube axially extends between a pair of ends and has a radially outward facing surface and a radially inward facing surface in which the radially inward facing surface defines a central passageway that places one of the pair of ends of the polymeric tube in fluid communication with the other one of the pair of ends of the polymeric tube. Each conductor axially extends between a pair of ends. The conductor has a polymeric sheath in which the polymeric sheath has a radially outward facing surface. The radially outward facing surface of the polymeric tube is bonded to the radially outward facing surface of the polymeric sheath of the conductor over an axial length except for at least one unbonded intermediate axial gap along this axial length. This or these unbonded intermediate axial gap(s) along this axial length exist between a pair of bonded sections and, in the unbonded intermediate axial gap(s), the radially outward facing surface of the polymeric tube is not bonded to the radially outward facing surface of polymeric sheath of the conductor thereby providing a starting point for subsequent manual separation of one of the ends of the polymeric tube from one of the ends the conductor.

In some forms, there may be a pair of unbonded intermediate axial gaps that are disposed proximate the pair of respective ends of the polymeric tube and the conductor. Because they are designed to provide starting points for separation of the ends, the pair of unbonded intermediate axial gaps may be close to the ends and, in one contemplated form, are within ten percent of the overall length of the tube and conductor set from the pair of respective ends.

In some forms, an axial length of the polymeric tube may be equal to the axial length of the conductor. Indeed, in cases where the tube and conductor set is continuously produced and periodically cut, the cut may establish the tube(s) and conductor(s) to be of equal length for a given set.

To facilitate bonding, the polymeric tube may comprise polyvinylchloride and the polymeric sheath of the conductor may comprise polyvinylchloride. Then upon application of focused heat, the polyvinylchloride may be selectively joined together over the axial length of the tube and conductor set.

In some forms, the tube and conductor set may comprises a pair of polymeric tubes including the aforementioned polymeric tube. Each of the pair of polymeric tubes may extend between a pair of ends and have respective radially outward facing surfaces and radially inward facing surfaces in which the radially inward facing surfaces define respective central passageways that place one of their respective pair of ends in fluid communication with the respective other one of their pair of ends. The radially outward facing surfaces of the pair of polymeric tubes may be bonded to one another along an axial length except for at least one unbonded intermediate axial gap along this axial length. The unbonded intermediate axial gap(s) between the polymeric tube and the conductor may occur along the same axial distance(s) as the unbonded axial gap(s) between the pair of polymeric tubes. When two or more tubes are present, the conductor may be bonded to only one of the polymeric tubes. Nonetheless, the conductor may be at least partially received or nest in a space between the radially outward facing surfaces of the pair of polymeric tubes. However, it is also contemplated that the conductor(s) might be placed elsewhere on the radially outward facing surface of the tube(s). For example, the axial length along which the conductor is bonded to the polymeric tube may be 90 degrees spaced on the polymeric tube from the axial length along which the pair of polymeric tubes is bonded to one another.

To keep the ends together and avoid damage during shipping, the axial length along which the pair of polymeric tubes is connected may include their respective pairs of ends. In this way, the ends are held together until a user manually separates the tube(s) and conductor(s).

In some forms, the conductor may be a multi-conductor including a plurality of conductors. Each of the plurality of the conductors in the multi-conductor may be separately sheathed and then may be further sheathed in the polymeric sheath of the conductor which is bonded to the radially outward facing surface of the polymeric tube.

It is contemplated that, in some forms, the conductor may be an electrical conductor and, in some forms, the conductor may be an optical conductor. In some sets, both electrical and optical conductors may be employed.

According to another aspect of the invention, a method of making a tube and conductor set from a polymeric tube having a radially outward facing surface and a radially inward facing surface and from a conductor having a polymeric sheath in which the polymeric sheath has a radially outward facing surface is disclosed. The method includes the step of bonding the radially outward facing surface of the conductor to the radially outward facing surface of the polymeric tube. The radially outward facing surface of the polymeric tube is bonded to the radially outward facing surface of the polymeric sheath of the conductor over an axial length except for at least one unbonded intermediate axial gap along this axial length between a pair of bonded sections. Along the at least one unbonded intermediate axial gap, the radially outward facing surface of the polymeric tube is not bonded to the radially outward facing surface of polymeric sheath of the conductor to provide a starting point for the subsequent manual separation of one of the ends of the polymeric tube from one of the ends the conductor.

The tube and conductor set may includes a pair of polymeric tubes including the polymeric tube in which the pair of polymeric tubes each have respective radially outward facing surfaces and radially inward facing surfaces. In this instance, the method may further include the step of bonding the radially outward facing surfaces of the pair of polymeric tubes to one another along an axial length except for at least one unbonded intermediate axial gap along this axial length. Again, as noted above, the unbonded intermediate axial gap(s) between the polymeric tube and the conductor may occur along the same axial distance as the unbonded intermediate axial gap between the pair of polymeric tubes.

In some forms, the method may further include the step of periodically cutting the polymeric tube and conductor to create an axial length providing the tube and conductor set after the step of bonding the radially outward facing surface of the conductor to the radially outward facing surface of the polymeric tube. The length of the tube and conductor set can include at least a pair of unbonded intermediate axial gaps along the axial length and, more preferably, a gap at each end.

In some forms, the method may further include the step of extruding the polymeric tube prior to the step of bonding the radially outward facing surface of the conductor to the radially outward facing surface of the polymeric tube.

It will be appreciated that the various features described herein might be used separately or in workable combinations with one another and the inclusion of any feature should not be read as the exclusion of another feature, where said features are compatible with one another. Thus, all workable combinations and permutations of the recited features should be considered as falling within the scope of this disclosure.

These and still other advantages of the invention will be apparent from the detailed description and drawings. What follows is merely a description of some preferred embodiments of the present invention. To assess the full scope of the invention, the claims should be looked to as these preferred embodiments are not intended to be the only embodiments within the scope of the claims.

DETAILED DESCRIPTION

Figure 1A:
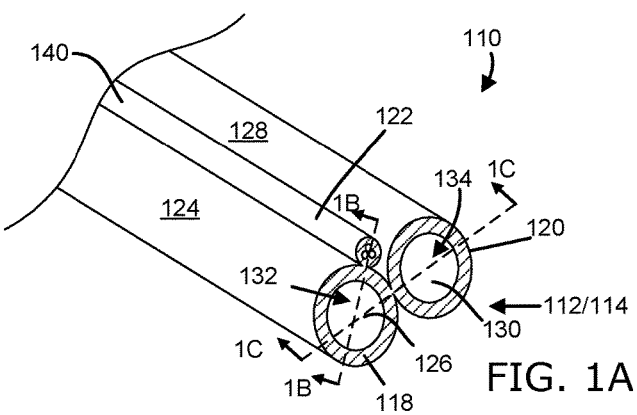
FIG. 1A is a perspective view of one end of a tube and conductor set having a pair of tubes and a conductor.
Figure 1B:
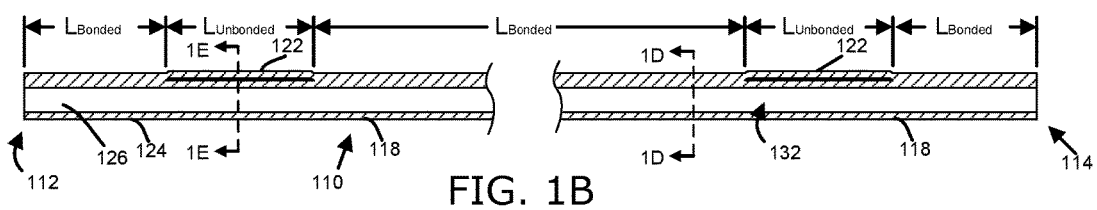
FIG. 1B is a cross-sectional view of the tube and conductor set of FIG. 1A taken through line 1B-1B through one of the tubes and the conductor.
Figure 1C:
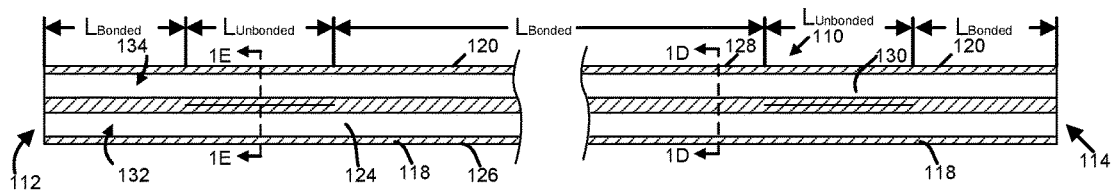
FIG. 1C is a cross-sectional view of the tube and conductor set of FIG. 1A taken through line 1C-1C through the pair of tubes.

Referring first to FIG. 1A-1E, a tube and conductor set 110 is illustrated. A tube and conductor set 110 of this type can be used to connect, for example, various parts of a medical device together to establish channels for fluid communication and/or establish pathways for electrical or optical communication for transmitting electrical or optical signals.

The tube and conductor set 110 axially extends between a pair of ends including a first end 112 and a second end 114 to define an overall axial length of the tube and conductor set 110. In many instances, the tube and conductor set 110 will be cut by the manufacturer to a pre-determined length (for example, ten feet); however, in some instances, the tube and conductor set 110 may be formed as a greater continuous length which can be cut to the desired length.

In the particular form illustrated in FIGS. 1A-1E, the tube and conductor set 110 includes a pair of polymeric tubes 116 including a first polymeric tube 118 and a second polymeric tube 120 and a conductor 122.

In the illustrated embodiment of FIGS. 1A-1E, the first polymeric tube 118 and the second polymeric tube 120 are identical to one another (although, if multiple tubes are part of the set, they may also be different from one another). The first polymeric tube 118 includes a radially outward facing surface 124 and a radially inward facing surface 126 and the second polymeric tube 120 includes a radially outward facing surface 128 and a radially inward facing surface 130, respectively. Each of the radially inward facing surfaces 126 and 130 define a central passageway 132 and 134, in the first and second polymeric tubes 118 and 120 respectively, that place one of the pair of ends of the respective tubes 118 and 120 with the other one of the pair of ends of the respective tubes. In the forms illustrated, the polymeric tubes comprise a polyvinylchloride (PVC) material that facilitates some flexure of the tube and conductor set 110 so that the tube and conductor set 110 can be coiled for packaging, shipping, or so forth.

As used herein, the phrases "radially inward facing" and "radially outward facing" are used to describe surfaces of an axially-extending body that either face toward the central axis of the body or that face away from the central axis of the body, respectfully. The term "radially" is used to generally indicate the facing of the surface with respect to the central axis and should not be understood as requiring a purely radial quality. Indeed, the axially-extending bodies to not need to be circular tubular or round and could instead be, for example, elliptical, square, rectangular, or any one of a number of other shapes and have still have surfaces with radially inwardly or outwardly facing components because these surfaces face toward or away from the central axis.

In the form illustrated, the conductor 122 is a multi-conductor including a plurality of separate conductors therein. In the particular form illustrated, the conductor 122 includes conductors 122a, 122b, and 122c which are separately protected by sheaths 136a, 136b, and 136c (which for electrical conductors can be electrically isolating). All three of these sheathed conductors 122a, 122b, and 122c are circumferentially surrounded by an outer polymeric sheath 138 so that the separately sheathed conductors 122a, 122b, and 122c run in parallel through the axial length of the outer polymeric sheath 138. In the forms illustrated, the outer polymeric sheath 138 comprises a polyvinylchloride (PVC) material and has a radially outward facing surface 140.

It should be appreciated that while a multi-conductor is illustrated in FIGS. 1A-1E, that the conductor 122 may be a single conductor sheathed by the outer polymeric sheath 138. Similarly, while three conductors are illustrated in the embodiment of FIGS. 1A-1E, it is contemplated that one, two, three, or more conductors may be part of the conductor or multi-conductor.

Looking in particular at FIGS. 1B through 1E, it can be seen that the tube and conductor set 110 includes various indicated axial lengths $L_{Bonded}$ and $L_{Unbonded}$. The axial lengths indicated as $L_{Bonded}$ are axial lengths over which the first and second polymeric tubes 116 and 118 are bonded to one another along their radially outward facing surfaces 124 and 128 and over which the radially outward facing surface 140 of the outer polymeric sheath 138 is bonded to at least the radially outward facing surface 124 of the first polymeric tube 116. The axial lengths indicated as $L_{Unbonded}$ are axial lengths over which the first and second polymeric tubes 116 and 118 are not bonded to one another along their radially outward facing surfaces 124 and 128 and over which the radially outward facing surface 140 of the outer polymeric sheath 138 is not bonded to at least the radially outward facing surface 124 of the first polymeric tube 116.

In the form illustrated, the entire length of the tube and conductor set 110 is bonded as designated by $L_{Bonded}$, except for a pair of unbonded intermediate axial gaps proximate the ends which are designed $L_{Unbonded}$. However, the most distal section of each of the respective ends 112 and 114 is bonded and the unbonded areas are slightly inwardly offset from the ends 112 and 114. Because the central portion of the length of the tube and conductor set 110 is bonded, this means that each of the unbonded intermediate axial gaps is between a pair of bonded sections.

Figure 1D:
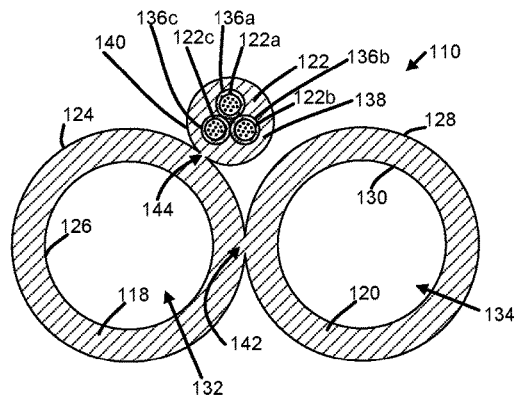
FIG. 1D is a cross-sectional view taken through line 1D-1D of FIGS. 1B and 1C in a region in which the tubes are bonded to one another and the conductor is bonded to one of the tubes.
Figure 1E:
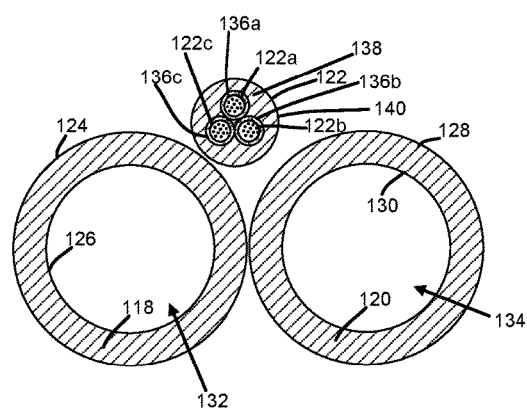
FIG. 1E is a cross-sectional view taken through line 1E-1E of FIGS. 1B and 1C in a region in which the tubes are not bonded to one another and the conductor is not bonded to one of the tubes.

FIGS. 1D and 1E provide cross sections taken perpendicular to the central axis in the bonded and unbonded regions, respectively. As can be seen in FIG. 1D, the bond 142 between the first polymeric tube 118 and the second polymeric tube 120 is a localized melted section extending in the axial direction between the first polymeric tube 118 and the second polymeric tube 120 which forms a separable linkage between the tubes 118 and 120. Similarly, the bond 144 between the first polymeric tube 118 and the conductor 122 is a localized melted section extending in the axial direction between the first polymeric tube 118 and the conductor 122 to form a separable linkage between the first polymeric tube 118 and the conductor 122. In FIG. 1E, which shows the unbonded sections, the bonds 142 and 142 are not present.

These unbonded intermediate axial gaps in the bonded between the tubes 118 and 120 and the conductor 122 provide a pre-defined region of separation in which a worker can easily insert their fingers and pull the tubes 118 and 120 and the conductor 122 toward the free end of the tube and conductor set 110. This separation of the tubes 118 and 120 and the conductor 122 is significantly easier than if the tubes 118 and 120 and the conductor 122 were bonded or fused over their entire length of the set because, in that instance, the ends would need to be pinched and pulled using the fingers of the user. Once the ends are separated, the separated ends may be trimmed to length, and then connectors or terminals can be attached to the various free ends of the tube(s) and conductor(s). However, prior to separation, the bonded end region keeps the ends together, which protects the ends from damage during shipping to the location of assembly.

It is contemplated that, instead of pulling the tubes 118 and 120 and the conductor 122 apart using the intermediate axial gaps, the tube and conductor set could alternatively be cut through the intermediate unbonded axial gaps to liberate the ends for subsequent processing via the cutting process. In fact, it is contemplated that a long length of the tube(s) and conductor(s) could be formed having various intermediate unbonded axial gaps and the action of cutting through these unbonded sections could both establish the free ends and establish the length of the cut segment.

Figure 2:
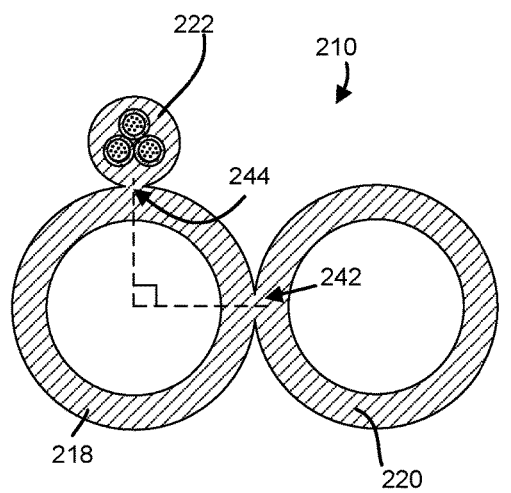
FIG. 2 is a cross-sectional view of a tube and conductor set similar to that illustrated in FIGS. 1A-1E, except that the conductor is differently connected to one of the tubes.

In the form illustrated in FIG. 1A-1E, the conductor 122 is disposed in a space between the bonded pair of tubes 118 and 120. Among other things, this helps to provide a compact profile for the tube and conductor set 110. However, it is contemplated that in other forms, the conductor could be placed differently. For example, in the alternative tube and conductor set 210 of FIG. 2 (which is shown only in cross section in a bonded region, but which would also have unbonded sections like those illustrated and described in the first embodiment shown in FIGS. 1A-1E), the tubes 218 and 220 are bonded at bond 242 and the conductor 222 is bonded at bond 244 to the tube 218 along axial lines that are 90 degrees spaced on the polymeric tube 218. However, other alternative spatial arrangements or configurations could also be employed.

Figure 3:
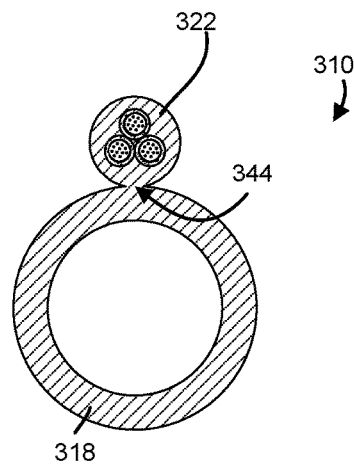
FIG. 3 is a cross-sectional view of a tube and conductor set in which there are only a single tube and a single conductor.

It should also be appreciated that, while a pair of polymeric tubes 116 are shown in the illustrated embodiment of FIGS. 1A-1E, it is contemplated that a tube and conductor set might include one, two, three, four, or more polymeric tubes. For example, FIG. 3 illustrates a bonded region of another alternative tube and conductor set 310 in which a single polymeric tube 318 is bonded to the conductor 322 along a bond 344. Although not illustrated, it can be readily appreciated that this single tube and single conductor arrangement would have unbonded sections similar to that illustrated in the form having two tubes and a conductor shown in FIGS. 1A-1E.

Figure 4:
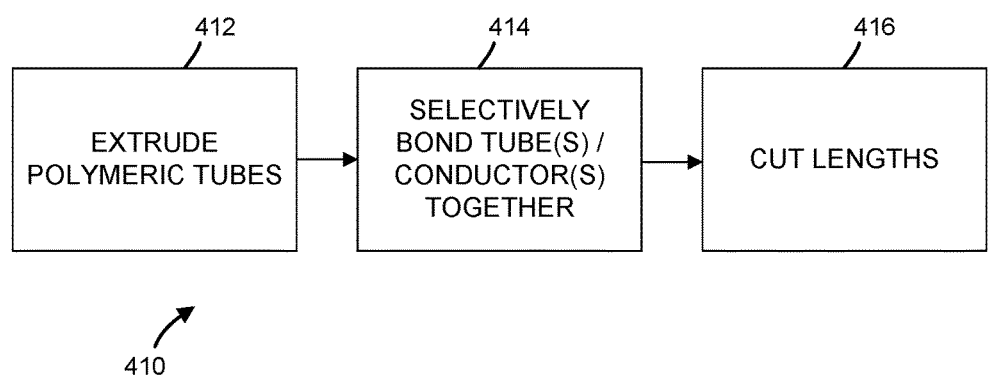
FIG. 4 is a schematic illustrating the method of making a tube and conductor set of the types disclosed herein.

Turning now to FIG. 4, a method 410 is illustrated for the production of tube and conductor set of the type described herein. First, in step 412, a polymeric tube or tubes are extruded from a polymer extruder machine. In a joining step or steps 414, the polymeric tube or tubes and a conductor or conductor(s) are then bonded according the desired spatial arrangement. This could be done, for example, using a heat gun or torch to locally melt and weakly bond the polymer of the outer surfaces of the tube(s) and conductor(s) to one another. The unbonded sections could be formed, for example, by periodically turning off the heat gun or torch or temporarily moving the heat gun or torch away from the tube(s) or the conductor(s). This bonding between the tube and tube and/or the tube and conductor could happen in a single step or multiple separate steps. Either before or after bonding, the combined tube and conductor set can also be periodically cut to a desired length in step 416.

It should be appreciated that various other modifications and variations to the preferred embodiments can be made within the spirit and scope of the invention. Therefore, the invention should not be limited to the described embodiments. To ascertain the full scope of the invention, the following claims should be referenced.

What is claimed is:

1. A tube and conductor set comprising:
   a polymeric tube axially extending between a pair of ends, the polymeric tube having a radially outward facing surface and a radially inward facing surface, the radially inward facing surface defining a central passageway that places one of the pair of ends of the polymeric tube in fluid communication with the other one of the pair of ends of the polymeric tube; and
   a conductor axially extending between a pair of ends, the conductor having a polymeric sheath in which the polymeric sheath has a radially outward facing surface;
   wherein the radially outward facing surface of the polymeric tube is bonded to the radially outward facing surface of the polymeric sheath of the conductor over an axial length except for at least one unbonded intermediate axial gap along this axial length between a pair of bonded sections and wherein, along the at least one unbonded intermediate axial gap, the radially outward facing surface of the polymeric tube is not bonded to the radially outward facing surface of polymeric sheath of the conductor to provide a starting point for subsequent manual separation of one of the ends of the polymeric tube from one of the ends the conductor.

2. The tube and conductor set of claim 1 wherein the at least one unbonded intermediate axial gap includes a pair of unbonded intermediate axial gaps that are disposed proximate the pair of respective ends of the polymeric tube and the conductor.

3. The tube and conductor set of claim 2 wherein the pair of unbonded intermediate axial gaps are within ten percent of the overall length of the tube and conductor set from the pair of respective ends.

4. The tube and conductor set of claim 1 wherein an axial length of the polymeric tube is equal to the axial length of the conductor.

5. The tube and conductor set of claim 1 wherein the polymeric tube comprises polyvinylchloride and wherein the polymeric sheath of the conductor comprises polyvinylchloride.

6. The tube and conductor set of claim 1 wherein the tube and conductor set comprises a pair of polymeric tubes including the polymeric tube, the pair of polymeric tubes each extending between a pair of ends and have respective radially outward facing surfaces and radially inward facing surfaces that define respective central passageways that placing one of their respective pair of ends in fluid communication with the respective other one of their pair of ends and wherein the radially outward facing surfaces of the pair of polymeric tubes are bonded to one another along an axial length except for at least one unbonded intermediate axial gap along this axial length.

7. The tube and conductor set of claim 6 wherein the at least one unbonded intermediate axial gap between the polymeric tube and the conductor occurs along the same axial distance as the at least one unbonded axial gap between the pair of polymeric tubes.

8. The tube and conductor set of claim 6 wherein the conductor is bonded to only one of the pair of polymeric tubes.

9. The tube and conductor set of claim 6 wherein the conductor is at least partially received in a space between the radially outward facing surfaces of the pair of polymeric tubes.

10. The tube and conductor set of claim 6 wherein the axial length along which the conductor is bonded to the polymeric tube along is 90 degrees spaced on the polymeric tube from the axial length which the pair of polymeric tubes are bonded to one another.

11. The tube and conductor set of claim 6 wherein the axial length along which the pair of polymeric tubes is connected includes their respective pairs of ends.

12. The tube and conductor set of claim 1 wherein the conductor is a multi-conductor including a plurality of conductors.

13. The tube and conductor set of claim 12 wherein each of the plurality of the conductors in the multi-conductor are separately sheathed and are further sheathed in the polymeric sheath of the conductor which is bonded to the radially outward facing surface of the polymeric tube.

14. The tube and conductor set of claim 1 wherein the conductor is an electrical conductor.

15. The tube and conductor set of claim 1 wherein the conductor is an optical conductor.

16. A method of making a tube and conductor set from a polymeric tube having a radially outward facing surface and a radially inward facing surface and from a conductor having a polymeric sheath in which the polymeric sheath has a radially outward facing surface, the method comprising:
bonding the radially outward facing surface of the conductor to the radially outward facing surface of the polymeric tube wherein the radially outward facing surface of the polymeric tube is bonded to the radially outward facing surface of the polymeric sheath of the conductor over an axial length except for at least one unbonded intermediate axial gap along this axial length between a pair of bonded sections and wherein, along the at least one unbonded intermediate axial gap, the radially outward facing surface of the polymeric tube is not bonded to the radially outward facing surface of polymeric sheath of the conductor to provide a starting point for subsequent manual separation of one of the ends of the polymeric tube from one of the ends the conductor.

17. The method of claim 16 wherein the tube and conductor set includes a pair of polymeric tubes including the polymeric tube in which the pair of polymeric tubes each have respective radially outward facing surfaces and radially inward facing surfaces and wherein the method further comprises the step of bonding the radially outward facing surfaces of the pair of polymeric tubes to one another along an axial length except for at least one unbonded intermediate axial gap along this axial length.

18. The method of claim 17 wherein the at least one unbonded intermediate axial gap between the polymeric tube and the conductor occurs along the same axial distance as the at least one unbonded intermediate axial gap between the pair of polymeric tubes.

19. The method of claim 16 further comprising the step of periodically cutting the polymeric tube and conductor to create an axial length providing the tube and conductor set after the step of bonding the radially outward facing surface of the conductor to the radially outward facing surface of the polymeric tube.

20. The method of claim 19 wherein the length of the tube and conductor set includes at least a pair of unbonded intermediate axial gaps along the axial length.

21. The method of claim 16 further comprising the step of extruding the polymeric tube prior to the step of bonding the radially outward facing surface of the conductor to the radially outward facing surface of the polymeric tube.

* * * * *